US009404897B2

(12) United States Patent
Oberdoerfer

(10) Patent No.: US 9,404,897 B2
(45) Date of Patent: Aug. 2, 2016

(54) METHOD FOR THE NON-DESTRUCTIVE INSPECTION OF A TEST OBJECT OF GREAT MATERIAL THICKNESS BY MEANS OF ULTRASOUND, THE USE OF A TEST PROBE FOR CARRYING OUT THE METHOD, AN ULTRASONIC TEST PROBE, A CONTROL UNIT FOR AN ULTRASONIC TEST PROBE AND A DEVICE FOR THE NON-DESTRUCTIVE INSPECTION OF A TEST OBJECT OF GREAT MATERIAL THICKNESS BY MEANS OF ULTRASOUND

(75) Inventor: York Oberdoerfer, North Rhine-Westphalia (DE)

(73) Assignee: GE Sensing & Inspection Technologies GMBH, Hurth (DE)

(*) Notice: Subject to any disclaimer, the term of this patent is extended or adjusted under 35 U.S.C. 154(b) by 719 days.

(21) Appl. No.: 13/611,181

(22) Filed: Sep. 12, 2012

(65) Prior Publication Data
US 2013/0080086 A1 Mar. 28, 2013

(30) Foreign Application Priority Data
Sep. 26, 2011 (DE) .................. 10 2011 053 942

(51) Int. Cl.
G01N 29/00 (2006.01)
G01N 29/34 (2006.01)
(Continued)

(52) U.S. Cl.
CPC .......... *G01N 29/262* (2013.01); *G01N 29/4463* (2013.01); *G01N 29/221* (2013.01); *G01N 2291/02854* (2013.01); *G01N 2291/106* (2013.01); *G01S 15/8922* (2013.01)

(58) Field of Classification Search
CPC . G01N 9/002; G01N 29/0645; G01N 29/262; G01N 2291/106; G01S 15/8922; G01S 7/5206; G01F 15/024; G01F 1/8436

USPC .......................................................... 702/56
See application file for complete search history.

(56) References Cited

U.S. PATENT DOCUMENTS 3,086,195 A 4/1963 Halliday
4,012,952 A 3/1977 Dory
(Continued)

FOREIGN PATENT DOCUMENTS

CN 1521501 A 8/2004
CN 101453679 A 6/2009
(Continued)

OTHER PUBLICATIONS

Unofficial English Translation of DE Office Action issued in connection with corresponding Application No. 102011053942.5 on Feb. 5, 2014.
(Continued)

*Primary Examiner* — Mischita Henson
*Assistant Examiner* — Christine Liao
(74) *Attorney, Agent, or Firm* — GE Global Patent Operation

(57) ABSTRACT

Method and apparatus for the non-destructive inspection of a test object with a large material thickness by means of ultrasound. The apparatus includes an ultrasonic test probe with an ultrasonic transducer divided into a plurality of individually activatable transducer segments wherein the transducer segments are concentric circles or rings, or sections thereof. A first group j (j=1, 2, 3, ...) of transducer segments is selected in such a way that a parallel activation of these transducer segments results in a circular active surface Fj of the ultrasonic transducer (22). An ultrasound inspection of the test object is undertaken with the first group j (j=1, 2, 3, ...) of transducer segments, wherein they are activated in parallel.

15 Claims, 8 Drawing Sheets

(51) Int. Cl.
  *G01N 29/26* (2006.01)
  *G01N 29/44* (2006.01)
  *G01N 29/22* (2006.01)
  *G01S 15/89* (2006.01)

(56) References Cited

U.S. PATENT DOCUMENTS

| | | | |
|---|---|---|---|
| 4,155,259 A | | 5/1979 | Engeler |
| 4,241,611 A | * | 12/1980 | Specht et al. ............... 73/626 |
| 4,276,779 A | | 7/1981 | Davis |
| 4,395,652 A | | 7/1983 | Nakanishi et al. |
| 4,462,082 A | * | 7/1984 | Thiele et al. ............... 702/103 |
| 4,487,073 A | | 12/1984 | Sumino |
| 4,537,074 A | * | 8/1985 | Dietz ............... 73/625 |
| 4,569,231 A | | 2/1986 | Carnes et al. |
| 5,533,401 A | * | 7/1996 | Gilmore ............... 73/622 |
| 5,931,785 A | * | 8/1999 | Mason ............... 600/459 |
| 6,120,454 A | | 9/2000 | Suorsa et al. |
| 2010/0212431 A1 | * | 8/2010 | Clossen-Von Lanken Schulz et al. ............... 73/632 |
| 2012/0060612 A1 | * | 3/2012 | Kleinert et al. ............... 73/632 |

FOREIGN PATENT DOCUMENTS

| | | |
|---|---|---|
| CN | 101712027 A | 5/2010 |
| DE | 1038309 B | 9/1958 |
| DE | 2709925 A | 10/1977 |
| EP | 2249152 A2 | 11/2010 |
| GB | 664763 A | 1/1952 |
| GB | 674235 A | 6/1952 |
| GB | 1572617 A | 7/1980 |
| JP | H0580037 A | 3/1993 |
| JP | 2009243890 A | 10/2009 |

OTHER PUBLICATIONS

Krautkramer et al., "Ultrasonic Testing of Materials", Springer, p. 59, 1990.

European Search Report and Written Opinion issued in connection with corresponding EP Application No. 12185278.4-1559 dated Feb. 28, 2014.

"EN 583-2:2001—Non destructive testing—Ultrasonic inspection—Part 2: Sensitivity and range settings", EN 583-2:2001, Oct. 1, 2001.

* cited by examiner

METHOD FOR THE NON-DESTRUCTIVE INSPECTION OF A TEST OBJECT OF GREAT MATERIAL THICKNESS BY MEANS OF ULTRASOUND, THE USE OF A TEST PROBE FOR CARRYING OUT THE METHOD, AN ULTRASONIC TEST PROBE, A CONTROL UNIT FOR AN ULTRASONIC TEST PROBE AND A DEVICE FOR THE NON-DESTRUCTIVE INSPECTION OF A TEST OBJECT OF GREAT MATERIAL THICKNESS BY MEANS OF ULTRASOUND

FIELD AND BACKGROUND OF THE INVENTION

The subject matter of the present invention is a method for the non-destructive inspection of a test object of great material thickness by means of ultrasound, the use of a test probe known per se for carrying out the method, an ultrasonic test probe particularly suitable for carrying out the method, a control unit for an ultrasonic test probe for the non-destructive inspection of a test object of great material thickness by means of ultrasound, which can, in particular, be configured for carrying out the method, and a device for the non-destructive inspection of a test object of great material thickness by means of ultrasound.

A variety of methods for the non-destructive inspection of a test object by means of ultrasound are known from the field of material testing. In the pulse echo methods, a short ultrasonic pulse generated by an ultrasonic transducer acting as a transmitter is suitably insonified into a test object so that it propagates in the test object. If the pulse hits a flaw in the test object, for example a discontinuity operated as a receiver, or a geometric structure, the pulse is reflected at least partially. The reflected pulse is detected by means of an ultrasonic transducer. An ultrasonic transducer is frequently used both as a transmitter as well as a receiver. The position of the discontinuity in the test object can be deduced from the travel time between the insonification of the pulse into the test object and the arrival of the reflected pulse at the receiver. The amplitude of the reflected pulse can be used to obtain information on the size of the discontinuity.

In standardized manual ultrasonic testing, two methods for assessing the size of a discontinuity have become established globally, i.e. the reference body method (also referred to in short as DAC method, from "distance-amplitude correction") and the DGS method (from "distance-gain-(flaw)size"). Both methods are different as regards application, but not with respect to the fundamental physics of sound propagation and sound reflection they are based on. In both methods, the examiner determines the size (diameter) of a model reflector (cylindrical reflector in the DAC method, circular disk in the DGS method). The size thus determined is, in principle, not identical to the actual flaw size; it is therefore referred to as equivalent circular disk or cross hole diameter. In case of the usage of circular disk reflectors the shorter term "equivalent reflector size" (ERS) has become established. That the actual flaw size does not correspond to the equivalent reflector size is due to the fact that the portions of the sound reflected by a natural flaw are additionally affected by the shape, orientation and surface properties of the flaw. Because further examinations in this respect are difficult and not very practicable in manual ultrasonic testing, the criteria for recording faults are tied to a certain equivalent reflector size in most specifications and guidelines for ultrasonic testing. This means that the examiner determines in practice whether a detected fault reaches or exceeds the equivalent reflector size specified as a threshold value (recording threshold) in the documentation. Beyond this, he generally will have to carry out further inspections, for example with regard to the recording length, echo dynamics etc., which, however, shall not be discussed here.

The laws of sound propagation in matter have long been theoretically known and were verified in practice by many experiments. The development of the modern assessment methods presents to ways: In the DAC method, the characteristics of the sound field are determined in each case prior to ultrasonic testing by means of a calibration measurement on a reference body; in contrast, the DGS method uses the theory in the form of the so-called DGS diagrams provided for the test probes. A DGS diagram shows the echo amplitudes of circular disk reflectors of different diameters and of a large flat reflector (back face) as a function of the distance.

For carrying out the DAC method, a reference body with one or more reference reflectors that corresponds to the test object must be provided for inspection. The dependency on distance of the echo amplitudes is experimentally determined by means of the bore holes present in the reference body, and transferred onto the display of the testing device as a curve. This curve automatically contains all influences of the test probe (sound field) and of the material. The test object can now be scanned with the ultrasonic test probe. A recordable indication is given if an echo reaches or exceeds the DAC curve.

The requirement for carrying out the DGS method is that the corresponding ultrasonic test probe-specific DGS diagram has to be provided for the ultrasonic test probe which is to be used for the inspection task. The equivalent reflector size is determined from the DGS diagram for the maximum echo of a detected flaw indication. It is thus possible to assess whether the indication is recordable or not.

The use of microprocessor-controlled ultrasonic devices results in considerable simplifications in both assessment methods, which lead to time being saved and a higher testing reliability. In particular, DGS assessment is simplified in a modern ultrasonic device by storing the DGS diagrams of standard test probes in the device. Preferably, a flat bottom hole (circular disk), a cross hole or a back face can be selected as a reference reflector. An evaluation program can provide for an immediate assessment of a detected flaw indication. In the process, the recording threshold exceedance, i.e. the dB value by which the flaw indication exceeds the predetermined recording curve, can be directly displayed on a display device, e.g. an integrated screen. This form of evaluation corresponds to the practice of most testing standards. These include, for example the well-known DIN EN 583-2, DIN 54 125 and SEL 072, but also all other specifications in which flat bottom holes are prescribed as reference reflectors.

Even though the above-mentioned pulse echo methods have been well-established methods in the field of material testing for years, their application to the inspection of test objects with a great material thickness, e.g. in the case of thick-walled pressure or safety tanks with a great wall thickness, today still requires a lot of effort. In the case of the DGS method, the reason for this is that an ultrasonic transducer generates a sound field which generally has several local sound pressure maxima located on the acoustic axis. The position of the last sound pressure maximum on the acoustic axis is in this case referred to as "near-field length N". For an ultrasonic transducer having a circular active surface with a diameter D (hereinafter referred to as "circular ultrasonic transducer"), the near-field length N is given by:

$$N = \frac{D^2}{4\lambda}$$

In this case, λ is the wavelength of the sound field in the test object material. In practice, it was found that a reliable echo evaluation is possible only if, viewed along the sound path, the distance of the defect from the insonification location is at least 70% of the near-field length N of the test probe used. If, for example, an ultrasonic test probe with a circular transducer is used, the latter must therefore have a small diameter D in order to assess defects close to the surface.

On the other hand, the sensitivity of a test probe decreases rapidly when the distance between the coupling location and the position of the flaw is doubled, owing to the divergence of the sound field propagating in the test object material. In the case of a ultrasonic test probe with a circular transducer, the divergence observed is substantially determined by the diameter D of the transducer, the rule being that large transducers have a smaller divergence than small ones. Because most testing standards for a size assessment of a flaw prescribe a minimum indication level, this results in the necessity, when inspecting test objects with a great material thickness, of using test probes with a large transducer diameter D in the inspection of sectors having a large distance from the coupling location, i.e. for the detection of deep flaws. However, they are not suitable for detecting defects close to the surface. In practice, a plurality of different test probes is therefore always used in the inspection of test objects with a great material thickness, such as, for example thick-walled cast containers or of long shafts. If a flaw is identified, an ultrasonic test probe is specifically selected for a quantitative flaw determination whose near-field length N is approximately in the range of the distance between the coupling location and the flaw position, with the above-mentioned criterion for the near-field length N having to be observed. A consequence of this is that, on the one hand, a plurality of different test probes has to be kept in storage, which increases the technical expenditure, on the other hand, a change of the test probe increases the inspection expenditure, which leads to cost disadvantages.

SUMMARY OF THE INVENTION

This is where the invention comes in, which has set itself the object of specifying a novel method for the non-destructive inspection of a test object of great material thickness by means of ultrasound, the use of a test probe known per se for carrying out the novel method, a novel ultrasonic test probe particularly suitable for carrying out the method, a novel control unit for an ultrasonic test probe for the non-destructive inspection of a test object of great material thickness by means of ultrasound, which is configured for carrying out the novel method, and a novel device for the non-destructive inspection of a test object of great material thickness by means of ultrasound.

This object is achieved by a method for the non-destructive inspection of a test object with a great material thickness by means of ultrasound, an ultrasonic test probe, a use of an ultrasonic test probe, a control unit for an ultrasonic test probe, as well as a device for the non-destructive inspection of a test object of great material thickness by means of ultrasound as described in the specification, claims, and drawings.

The method according to the invention is provided for the non-destructive inspection of a test object with a great material thickness by means of ultrasound. In its simplest form, the method according to the invention is based on providing an ultrasonic test probe basically known from the prior art, which comprises an ultrasonic transducer that is in turn divided into a plurality of individually activatable transducer segments. In this case, the transducer segments form concentric circles or rings, or they are sections of concentric circles or rings. In the prior art, such a transducer is referred to as "annular array" or "ring array". With respect to further technical details, reference is made to the standard DIN EN 16 018 (2011).

Improvements are the result of using the test probes according to the invention, which are also described below.

According to the invention, a first group j (j=1, 2, 3, . . . ) of transducer segments of the ultrasonic transducer are activated in parallel in such a manner that the result is a circular active surface Fj of the ultrasonic transducer that can function as an ultrasound transmitter and receiver. An ultrasonic inspection of the test object is then carried out with this circular "effective" ultrasonic transducer. The inspection can be carried out, for example, in accordance with the pulse echo methods known from the prior art.

The method according to the invention permits controlling the sound field generated by an ultrasonic test probe with an annular array and thus adapt it to the specific inspection task by controlling the diameter of the active surface of the ultrasonic transducer. In the context of the present invention, the active surface is considered to be the surface of the ultrasonic transducer that participates as a transmitter in generating the ultrasound when the transducer is activated, or which participates as a receiver in generating the signal when the transducer is activated.

So far, only the phase-accurate activation of all transducer segments of an annular array is known from the prior art in order to achieve a shaping of a beam, such as focusing/defocusing. In contrast thereto, it is proposed according to the invention to specifically activate only a partial set of the transducer elements, with the activation taking place in a phase-locked manner, in particular without a phase shift between the transducer elements. Accordingly, the beam is controlled through changing the diameter of the active surface of the ultrasonic transducer. Therefore, the method according to the invention permits carrying out, with only a single ultrasonic test probe, standardized inspection methods, such as in accordance with EN DIN 583-2, which do not provide for the use of phased array test probes, even on test objects with a great material thickness for which a plurality of different test probes had to be used so far.

Many inspection tasks require certain criteria K to be satisfied so that the result of the ultrasound inspection can be considered to be reliable. These criteria are generally dependent on the specific inspection task, on the test object properties, the ultrasonic test probe used, and on the properties of, or the flaws in, the test object that are to be detected. In a preferred embodiment of the method according to the invention, the group of the transducer segments activated in parallel is therefore specifically selected in such a way that the ultrasonic field generated by the active (circular) surface of the ultrasonic transducer satisfies a criterion K to be observed for the specific inspection task.

By way of example, mention is made here of the ultrasonic inspection of a test object with a great material thickness by means of the DGS method. Ultrasonic test probes with a circular ultrasonic transducers are used within the context of the DGS method. As explained above, they have a near-field length N that is dependent upon the diameter D of the active surface of the ultrasonic transducer. If the minimum distance of the sector R to be inspected from the coupling location of the ultrasound along the sound path in the test object is designated with d when carrying out the inspection method, then the ultrasonic inspection of the sector R requires that a predetermined criterion K relating to the near-field length N and the minimum distance d be satisfied.

In connection with the ultrasound inspection by means of the method according to the invention based on the DGS method, the satisfaction of the following criterion K is particularly preferred:

$$K: d \geq 0.7 \times N$$

with d being the minimum distance of the sector R to be inspected from the coupling location of the ultrasound into the test object along the sound path in the test object.

Thus, if the inspection is carried out in accordance with the DGS method, the method according to the invention is based on the diameter of the active surface of the transducer segment being specifically set, by parallel activation of a plurality of transducer segments, in such a way that the above-mentioned criterion for the specific task is satisfied.

Of course, a specific inspection task can basically also require that other criteria are also met. For example, DIN EN 583-2 demands a sufficient signal level over the background signal, which implies that the diameter D of the active surface of the ultrasonic transducer should be as large as possible without, however, violating the first criterion.

In another preferred development of the method of the present invention, the sector Rj to be inspected of the test object is first selected in another method step. Then, in another step, the first group j (j=1, 2, 3, ...) of transducer segments is selected in such a way that in the case of a parallel activation of these transducer segments, the ultrasonic field generated by the active surface Fj of the ultrasonic transducer satisfies the criterion K. The ultrasonic inspection of the test object is then carried out with the selected group.

In an alternative embodiment of the method the ultrasound inspection is carried out in accordance with the DAC method.

In a particularly advantageous embodiment of the method according to the invention, the material thickness S to be inspected of the test object is preset, e.g. by input from the user. The material thickness S to be inspected of the test object is then divided into a plurality of sectors Ri (i=1, 2, 3, ...) disposed one behind the other in the ultrasound propagation direction in the test object. Preferably, these sectors Ri have substantially the same extent s (hereinafter referred to as "thickness") in the sound propagation direction. Finally, the sector Rj to be inspected is specifically selected from amongst the sectors Ri. For this purpose, a sector of the test object can be experimentally identified in advance, for example within the context of qualitative preliminary examinations of the test object, which is then to be subjected to a more specific inspection by means of the method according to the invention, e.g. for quantitative flaw analysis.

Moreover, it is also possible that the method according to the invention is carried out for different sectors Rj,k (j≠k), i.e. that at least a first and a second ultrasound inspection are carried out. In particular, it may be provided that the first and the second ultrasonic inspections are carried out from the same coupling location. Electronic screens, for example, can be used for acquiring different sectors Rj,k of the test object. Also in this case, the inspected sectors Rj,k have substantially preferably the same thickness sj=sk in the sound propagation direction.

In another advantageous embodiment of the method, it is provided that the transducer segments of the ultrasonic transducer of the provided ultrasonic test probe are dimensioned in such a way that the diameter Dm of the circular acoustically active surface Fm of the ultrasonic transducer formed by a selected group m of transducer segments is substantially proportional to the square root of m. The consequence of this, on the one hand, is that the near-field length Nm of the transducer with the active surface Fm, which increases by the square of the diameter Dm, is proportional to the ordinal number m of the selected group of transducer segments. This can be advantageous, in particular, in connection with the so-called DGS method because the criterion K: d≥0.7×N has to be observed. In that case, it is then readily possible to divide the material thickness S to be inspected of the test object into sectors Ri (i=1, 2, 3, ...) of the same thickness in accordance with the division of the ultrasonic transducer into transducer elements which are connected in parallel in a successive sequence in order to form a linearly increasing transducer surface.

Moreover, special advantages relating to the properties of the ultrasonic field used for ultrasound inspection can be realized if the individually activatable transducer segments substantially have the same surface f. If these transducer segments are excited as transmitters in parallel with the same amplitude, the result is a homogenous sound pressure distribution over the entire active transducer surface. Thus, the transducer elements activated in parallel, which form an acoustically active surface with the diameter D, generate the same sound field as a single-part circular ultrasonic transducer with the same diameter D.

In connection with the use of the DGS method, it has furthermore proved to be advantageous if the specific DGS diagram for the ultrasonic transducer having the circular active surface Fj formed by the selected group j of transducer segments is computed from the general DGS diagram of a single-part circular ultrasonic transducer. This makes programming a control unit for the ultrasonic test probe to be used within the context of the method particularly easy, because only the general DGS diagram has to be stored in the control unit, as well as an instruction relating to the conversion into the specific DGS diagrams of the ultrasonic transducers having the circular active surface Fj (j=1, 2, 3, ...).

An ultrasonic test probe according to the invention for the non-destructive inspection of a test object of great material thickness by means of ultrasound comprises an ultrasonic transducer divided into a plurality of individually activatable transducer segments. The transducer segments have the shape of concentric circles or rings, or the shape of sections of concentric circles or rings. According to the invention, the transducer segments are dimensioned in such a way that the diameter Dm of the circular active surface Fm of the ultrasonic transducer formed by a group m (m=1, 2, 3, ...) of transducer segments is substantially proportional to the square root of m. As was already explained in connection with the method according to the invention, the consequence of this is that the near-field length Nm of the transducer with the active surface Fm (which increases by the square of the diameter Dm of this transducer) is proportional to the ordinal number m of the selected group of transducer segments, which can be advantageous in particular in connection with the DGS method. Reference is made to the explanations in this regard.

Reference is also made to the explanations in respect of the method claim 13 that relates to an advantageous embodiment of the method, which is based on an ultrasonic transducer whose transducer segments substantially the same surface f.

It was further found in connection with the present invention that, in particular, an annular array which is known per se from the prior art can advantageously be used in order to carry out the method according to the invention, whereby the technical expenditure for introducing the method can be reduced.

A control unit for an ultrasonic test probe for the non-destructive inspection of a test object of great material thickness by means of ultrasound, which is advantageous for carrying out the present invention, is provided for activating an ultrasonic test probe comprising an ultrasonic transducer divided into a plurality of individually activatable transducer segments. In this case, the transducer segments are concentric circles or rings, or sections thereof. According to the invention, the control unit is configured to activate in parallel a first group j (j=1, 2, 3, ...) of transducer segments of the ultrasonic transducer in such a manner that the total result is a circular active surface Fj of the ultrasonic transducer.

In a particularly preferred embodiment, the control unit is furthermore configured for executing an ultrasonic inspection method during whose execution a predetermined criterion K has to be satisfied which is dependent upon the ultrasonic field that is generated by the acoustically active surface Fj of the ultrasonic transducer. For this purpose, the control unit is configured to select, taking into account the criterion K, a first group j (j=1, 2, 3, ...) of transducer segments whose parallel activation continues to result in a circular active surface Fj of the ultrasonic transducer, and the ultrasonic field generated by the active surface Fj of the ultrasonic transducer satisfies the criterion K.

Finally, the control unit, in further advantageous embodiments, can be configured to be able to carry out the advantageous embodiments of the method discussed in connection with the method according to the invention, particularly the optional further method steps. This particularly applies also if these advantageous embodiments of the method are based on the use of advantageous developments of the test probes with an annular array known from the prior art.

The invention moreover includes an advantageous device for the non-destructive inspection of a test object by means of ultrasound. On the one hand, this device comprises an ultrasonic test probe with an ultrasonic transducer divided into a plurality of individually activatable transducer segments, wherein the transducer segments are concentric circles or rings, or sections thereof, i.e. the ultrasonic transducer is configured as an annular array. On the other hand, the device comprises a control unit according to the invention. Thus, the device is suitable for carrying out the method according to the invention using an annular array known per se, whereby the advantages already described above in connection with the method in its various embodiments can be realized.

Further features and advantages of the method according to the invention, of the use according to the invention of a test probe known per se from the prior art, of the test probe according to the invention, of the control unit according to the invention, and of the device according to the invention become apparent from the dependent claims and the exemplary embodiments which are explained below. It is noted that the features of the subject matters of the dependent claims as well as the features of the exemplary embodiments can be freely combined with one another within the context of what is technically possible and feasible. Moreover, it is noted that the exemplary embodiments are not to be understood to be limiting, but are to serve for illustrating the present invention.

DETAILED DESCRIPTION OF THE INVENTION

Figure 1:
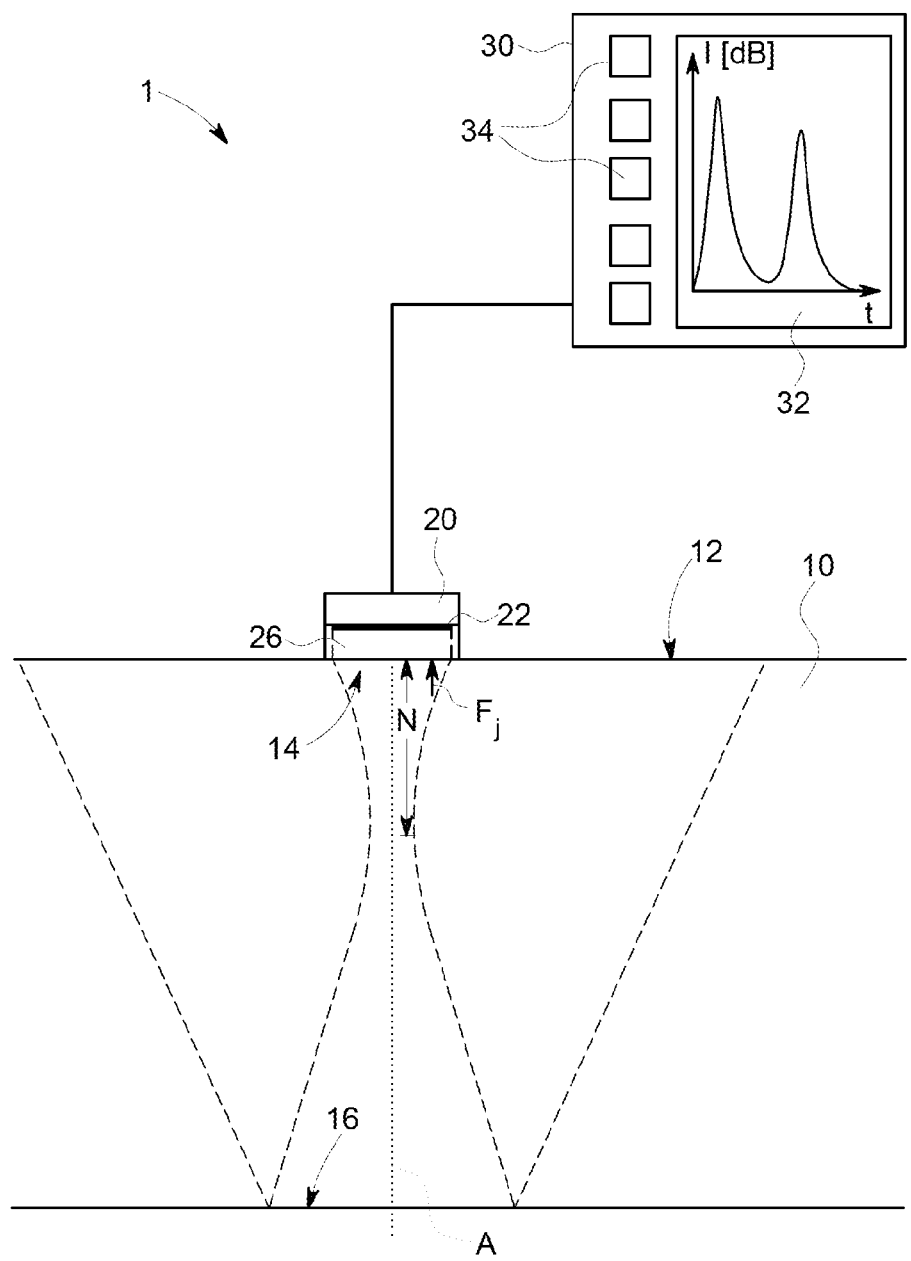
FIG. 1: shows schematic representation of a device according to the invention including a sectional view of a test object to be inspected.

The device 1 shown schematically in FIG. 1 serves for the non-destructive inspection of a test object by means of ultrasound, wherein the test object 10 can have, in particular, a great material thickness S to be inspected. The device 1 comprises a control unit 30 which is electrically connected to an ultrasonic test probe 20. In turn, the ultrasonic test probe 20 comprises an ultrasonic transducer 22 disposed on a suitable leading body 26 which is provided to be placed upon a surface of the test object 10, which is hereinafter referred to as the coupling surface 12. The leading body 26 serves as a protection against wear and for acoustically coupling the ultrasonic transducer 22 to the test object 10; it can consist, for example, of Plexiglass®. In this case, the ultrasonic test probe 20 can be configured in such a way that it is manually guided by an examiner over the coupling surface 12 of the test object 10 so as to obtain information on structures in the material of the test object 10 in the process. The ultrasonic transducer 22 is divided into a plurality of individually activatable transducer segments 24, which are either are circular or annular, or constitute sections of circular or annular transducer elements.

Figure 2:
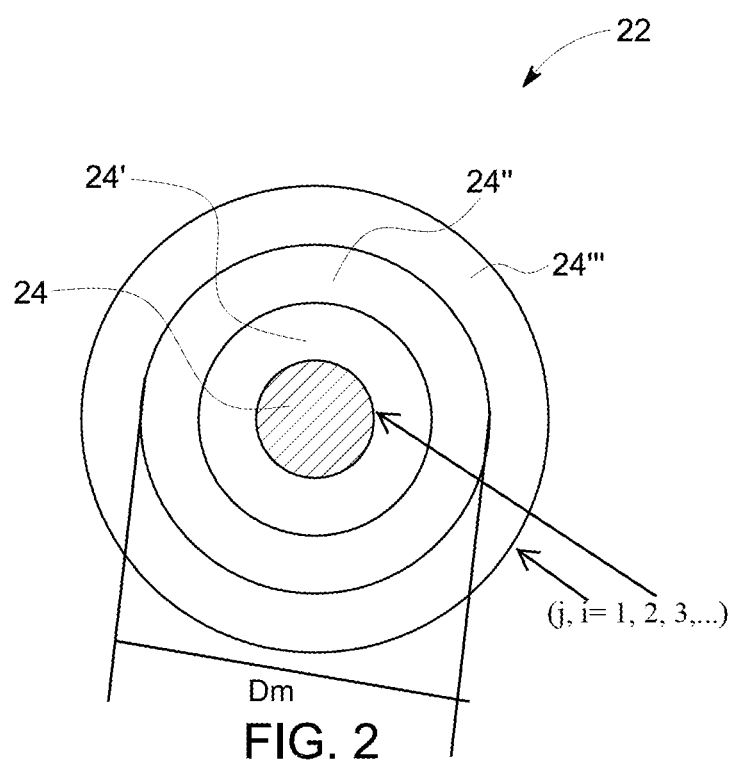
FIG. 2: shows a top view of the ultrasonic transducer of an ultrasonic test probe according to a first preferred embodiment.

By way of example, FIG. 2 shows the segmented ultrasonic transducer 22 of an ultrasonic test probe 20, which is basically known from the prior art, but which has proved to be particularly suitable for use within the context of the method according to the invention proposed herein. The transducer segments 24 of the ultrasonic transducer 22 according to FIG. 2 are in this case configured to be annular, with the exception of the central transducer segment 24, which is circular. The radius r of the central transducer segment 24 in this case matches the ring width S of the subsequent transducer segments 24, 24', 24" and 24'''. All transducer segments 24, 24', 24" and 24''' are electrically insulated from one another and separately activatable. In the context of the method according to the invention, different groups of transducer segments are jointly activated, so that the result in each case is an ultrasonic transducer 22 with a circular active transducer surface having the diameter Dj. The surface of the circular insulating areas situated between the transducer segments 24, 24', 24", 24''' which electrically insulate the different transducer segments 24 from each other, are in this case configured so as to be negligibly small relative to the surface of the individual transducer segments 24, 24', 24", 24'".

However, the ultrasonic transducer 22 can consist, for example, of a plate-shaped piezo-electric material which is provided with a metallic electrode on the top and the bottom. In order to form the independently activatable transducer segments, this electrode can be patterned at least on one of the two covering surfaces of the plate-shaped transducer material in order to form electrode areas that are electrically insulated from one another.

The control unit 30 shown in FIG. 1, which is electrically connected to the ultrasonic test probe 20, is configured for carrying out the method according to the invention. Referring to the ultrasonic transducer 22 apparent in FIG. 2, the control unit 30 is thus configured to select from the set of the transducer segments 24, 24', 24",24'" a group j (j=1, 2, 3, 4) whose parallel activation results in a circular active surface (F1, F2, F3, F4) of the ultrasonic transducer 22. In the exemplary embodiment shown here, the first group (j=1) consists of the transducer segment 24, the second group (j=2) of the transducer segments 24 and 24', the third group (j=3) of the transducer segments 24, 24' and 24", and the fourth group (j=4) of the transducer segments 24, 24', 24" and 24'". If the diameter D1 of the central transducer segment 24 with the surface F1: D1=2×r, then the diameter D2 of the active circular surface F2: D2=4×r, the diameter D3 of the active surface F3: D3=6×r, and the diameter D4 of the circular active surface F4: D4=8×r.

The following exemplary values for the near-field length N of the emerging "effective ultrasonic transducers" are obtained for the ultrasonic transducer 22 according to FIG. 2, for an ultrasound frequency of 2 MHz and a sound velocity in the test object of 5920 m/s.

| Transducer elements | Diameter D of acoustically active surface [mm] | Near-field length [mm] |
| --- | --- | --- |
| 24 | 10 | 8 |
| 24, 24' | 20 | 34 |
| 24, 24', 24" | 30 | 76 |
| 24, 24', 24", 24'" | 40 | 135 |

After a first group j, for example the group j=1 consisting of the single transducer segment 24, was selected by the control unit 30, the control unit 30 activates exclusively this single transducer segment 24. This transducer segment 24 then generates a sequence of short ultrasonic pulses that propagate through the leading body 26 and enter the material of the test object 10 via the coupling surface 12. In the material of the test object 10, the ultrasonic pulses propagate along the acoustic axis A indicated in FIG. 1. If the ultrasonic pulses in the material of the test object 10 hit, for example, a discontinuity or a back face of the test object, which is designated 16 in FIG. 1, they are reflected back and return to the test probe 20. Its ultrasonic transducer 22 then acts as a receiver, records the reflected pulses as pulse echoes, converts them into electrical signals and transmits them to the control unit 30. In the control unit 30, the received echo signals are processed, for example amplified and filtered, and displayed on a display device 32, which in the exemplary embodiment shown is integrated into the housing of the control unit 30. FIG. 1 shows a so-called A-scan on the display device 32, in which the recorded echo amplitude is plotted over the time. The operating elements 34 provided on the control unit 30 serve for the operation of the control unit 30 by a user, for example by means of a menu.

Figure 4:
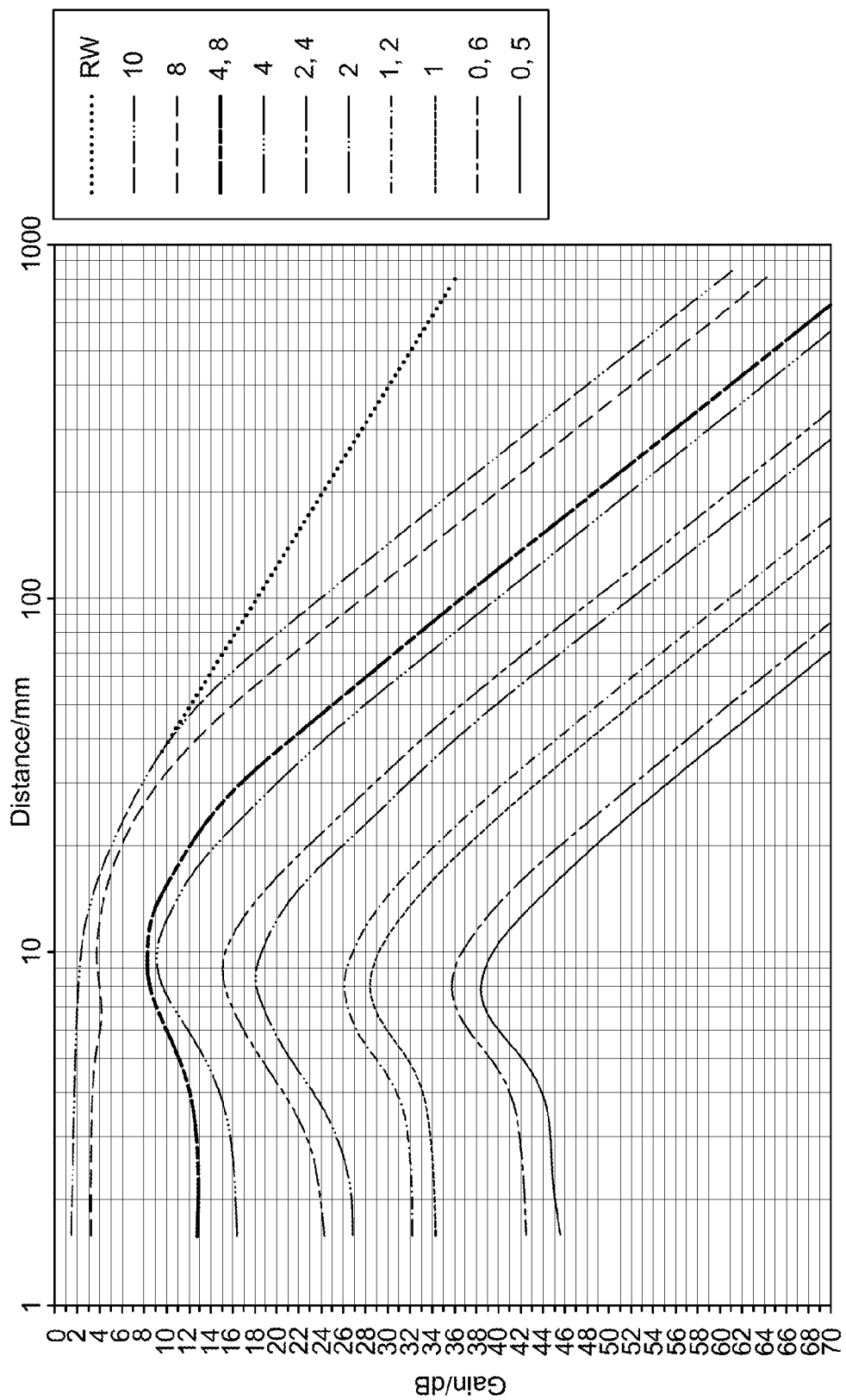

If a rotationally symmetric ultrasonic field is presumed as it is generated, for example, by a circular ultrasonic transducer, and if one determines the echo amplitude of a reference flaw in the shape of a planar circular disk which is perpendicularly exposed to sound, then plots the maximum echo amplitude as a function of the distance of the reference flaw from the insonification location in a diagram (or, equivalently, the gain factor required to amplify the received echo amplitude to a predetermined signal level), and if one repeats this process for reference flaws of different diameters, then one obtains the so-called DGS diagram. This is characteristic for the ultrasonic test probe used, in this case particularly for the diameter of the acoustically active area of the ultrasonic transducer, as well as the acoustic properties of the test object material. By way of example, FIG. 4 shows a DGS diagram for a reference flaw (circular disk with a diameter of 10 mm) for the test probe 20, which uses the ultrasonic transducer 22 shown in FIG. 2, with only the central transducer element 24 being activated in this case. It can be seen clearly that a clearly defined maximum of the echo amplitude results for virtually all flaw sizes. This substantially coincides with the near-field length N of the ultrasonic test probe used.

As was already explained in the introduction, the near-field length N is determined by the position of the last sound pressure maximum on the acoustic axis. If measurements are now carried out in accordance with the so-called DGS method, it was found that the inspection results found by means of the DGS method have a high degree of reliability and reproducibility if the following criterion K is observed:

$$K: d \geq 0.7 \times N$$

wherein d denotes the depth of the detected flaw in the test object material along the acoustical axis A. Therefore, if one desires to be able to detect flaws close to the surface, then a test probe with a short near-field length has to be used in the case of the DGS method, i.e. a test probe whose circular ultrasonic transducer has a small diameter D. However, as is also apparent from the DGS diagram according to FIG. 4, once the maximum has been passed in the vicinity of the near-field length N, the maximum echo amplitude drops significantly as the distance between the coupling location and the flaw increases. Thus, if an ultrasonic test probe with a small near-field length is used for measurement according to the DGS method, only a small echo amplitude is obtained for flaws that a located deep in the material of the test object. However, many inspection standards prescribe the exceedance of a minimum recording limit for flaw detection for an effective ultrasound inspection, which is no longer possible as a matter of principle with an ultrasonic test probe having a small near-field length, due to the underlying physical properties of the ultrasonic field used for inspection. In order to inspect deeper sectors of the test object, the examiner until now had to switch to an ultrasonic test probe in practice whose near-field length was greater than the near-field length of the first ultrasonic test probe. Since the following now applies for the near-field length:

$$N = \frac{D^2}{4\lambda},$$

wherein λ is the wavelength of the sound field in the test object material and D is the diameter of the circular ultrasonic transducer of the test probe, the ultrasonic transducer of this second test probe must have a larger diameter than that of the first test probe. If even deeper sectors of the test object are to be inspected, a third, a fourth, a fifth etc. ultrasonic test probe had to be used, wherein the diameter D of the ultrasonic test probes used had to increase continuously. On the one hand, this mandatory change of test probes was time-consuming and therefore entailed cost disadvantages, on the other hand, a change of test probes is always accompanied by systematic measuring errors, which are also disadvantageous.

It is exactly these drawbacks that the use proposed according to the invention of the test probe 20 according to the first exemplary embodiment, whose ultrasonic transducer is shown in FIG. 2, avoids. By way of example, FIG. 3 indicates the ultrasonic field 28 forming in test object 10 which is generated by the test probe 20 when the control unit 30 excites exclusively the central transducer segment 24 to emit ultrasonic pulses. The near-field length N1 of this first "effective ultrasonic test probe", which is just underneath the coupling surface 12 in the material of the test object 10, is drawn into FIG. 3. The position d1 on the acoustic axis A in which the above-mentioned criterion K1: d1≥0.7×N1 is satisfied for this first effective ultrasonic test probe 20 is also drawn in. A valid ultrasound inspection is possible with this first effective ultrasonic test probe 20 in the sector R1 of the test object 10 in which the aforementioned criterion is satisfied.

Figure 3:
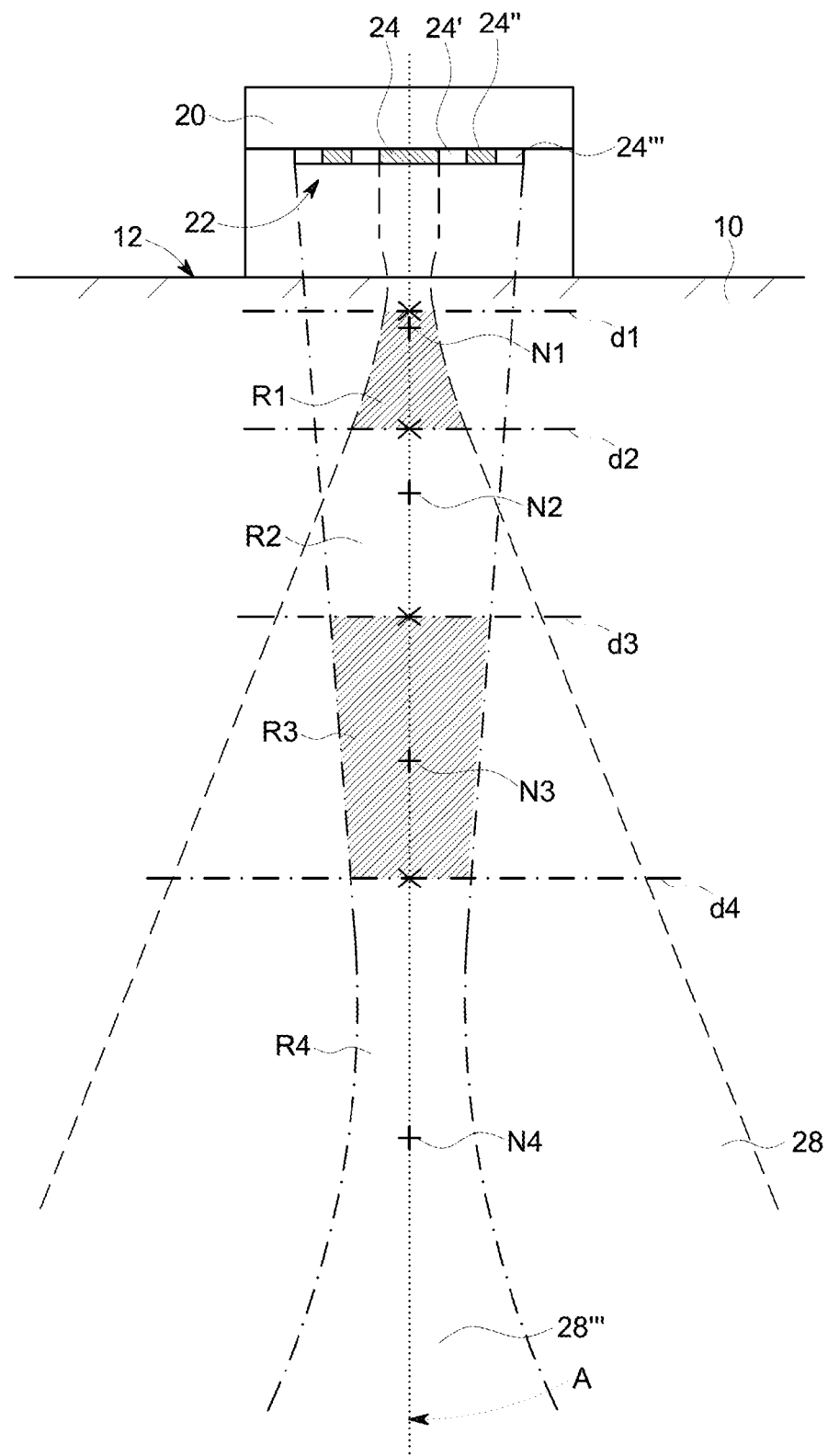
FIG. 3: shows an enlarged detail from FIG. 1, FIG. 4: shows a DGS diagram for the ultrasonic test probe with the ultrasonic transducer shown in FIG. 2 for a reference flaw having a diameter of 10 mm.

Furthermore, FIG. 3 indicates the ultrasonic field 28''' which is obtained if all transducer segments 24, 24', 24'' and 24''' of the ultrasonic transducer 22 are activated in parallel. The near-field length N4 that forms lies deep in the material of the test object 10; the aforementioned criterion K4: d4≥0.7× N4 is also satisfied for a significantly deeper sector R4.

Furthermore, the near-field lengths N2 and N3 of those effective ultrasonic test probe 20 are drawn into FIG. 3 which are obtained if the transducer segments 24 and 24' (N2), or the transducer segments 24, 24' and 24'' (N3), are activated in parallel. The positions d2 and d3 at which the respective criteria K2 and K3 for the effective ultrasonic test probes 20'', 20''' are satisfied are also drawn in.

In practice, it was now found that the best possible combination of maximum flaw amplitude and the highest degree of reliability or reproducibility of the ultrasound inspection is obtained if, for the ultrasound inspection, the material of the test object 10 is divided along the acoustic axis into virtual sectors R1, R2, R3, R4, wherein the sector R1 extends from the depth d1=0.7×N1 to the depth d2=0.7×N2, the sector R2 from the depth d2=0.7×N2 to d3=0.7×N3 etc. The sectors R1, R2, R3 and R4 thus obtained are indicated in FIG. 3 by a hatched pattern.

Figure 5:
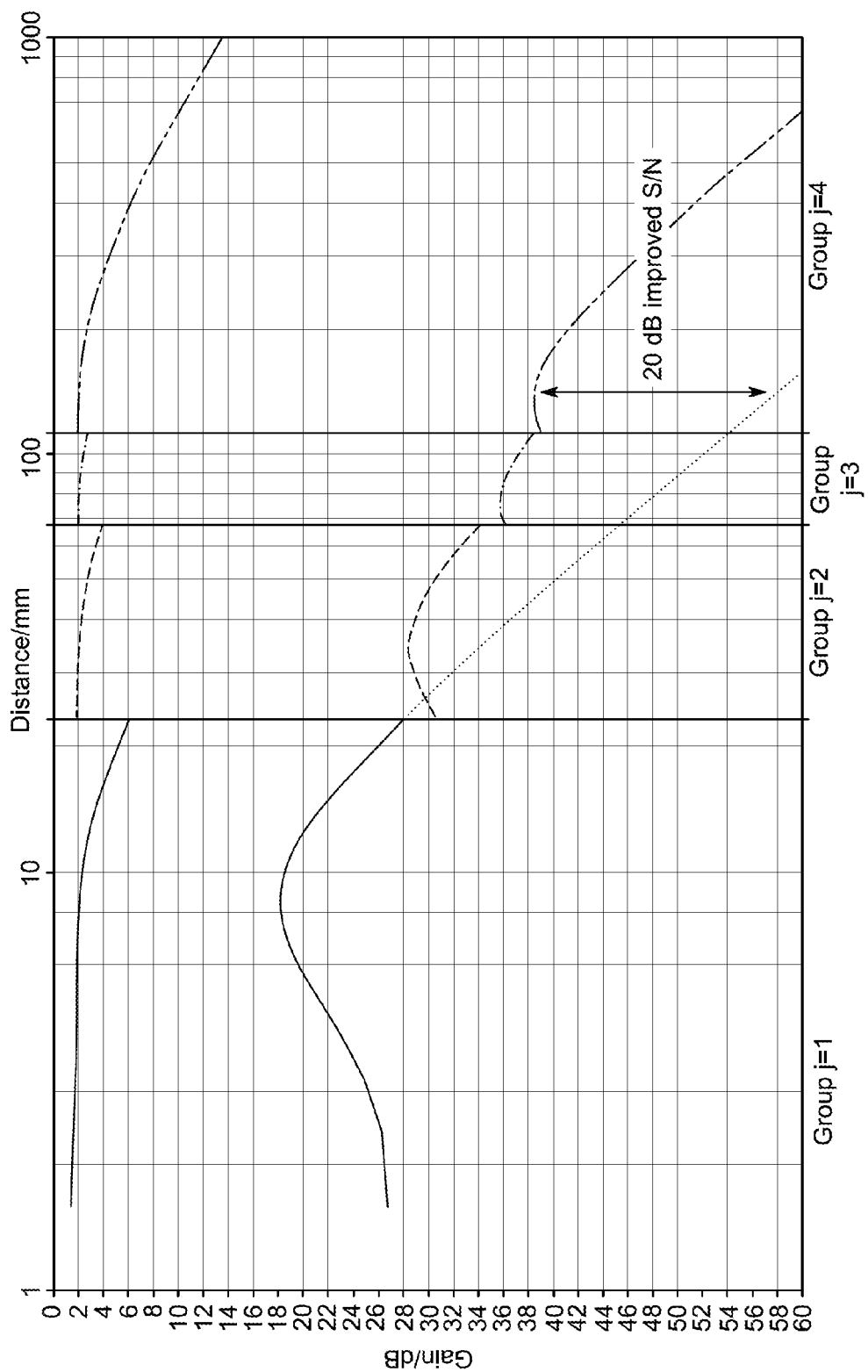
FIG. 5: shows an "effective" DGS diagram for the ultrasonic test probe with the ultrasonic transducer shown in FIG. 2 for a reference flaw having a diameter of 10 mm.

By a specific variation of the diameter D of the acoustically active surface of the ultrasonic transducer 22, the present invention thus permits varying the near-field length N of the ultrasonic test probe 20 so that different sectors R of the test object 10 can be specifically inspected by means of the DGS method under optimum conditions. The DGS diagram of such an ultrasonic test probe 20 with a variable transducer diameter D results from the superposition of the DGS diagrams of the different effective ultrasonic test probes 20 with their respective effective transducer diameters. Such a DGS diagram is shown by way of example in FIG. 5 for the ultrasonic test probe 20 according to the first exemplary embodiment based on the ultrasonic transducer 22 according to FIG. 2. Here, the back-face echo and the echo amplitude are shown that are obtained for a reference flaw with a diameter of 2 millimeters. For the purpose of illustration, the profile of the echo amplitude for the selected reference flaw is shown for the first effective test probe 20 with the smallest transducer diameter D1 for a large depth range. The sharp drop in sensitivity for larger distances d from the coupling location 14 (as shown in FIG. 1) if only the effective small transducer diameter D1 is used can be clearly seen. Moreover, the significant improvement of the signal amplitude becomes visible which can be obtained by the second effective ultrasonic test probe 20' (whose transducer 22' is formed by the transducer segments 24 and 24') being activated while the criterion K2: d2≥0.7×N2 is satisfied. This is also indicated for the third and fourth effective ultrasonic test probes 20'', 20'''. In this manner, an increase of the signal amplitude by up to 20 decibel can be achieved as compared with the first effective ultrasonic test probe 20, which would otherwise only be possible by changing the ultrasonic test probe.

The transducer configuration with annular transducer segments 24 of a continuous ring width r shown in FIG. 2 in this cases substantially serves for illustrating the present invention. Another criterion which, however, advantageously is to be observed when carrying out inspection tasks by means of the DGS method is that the sound field generated by a segmented ultrasonic transducer 22 formed by several transducer segments 24, 23', 24'', 24''' etc. that are activated in parallel must be substantially identical to the sound field which would be generated by a single-part circular ultrasonic transducer 22 with the same diameter D and surface. In the case of a segmented ultrasonic transducer 22, this can be achieved by all transducer segments 24 oscillating with the same amplitude during sound generation. It was now found that the aforementioned condition is satisfied if all transducer segments 24 have substantially the same electrical capacitance. As a rule, the transducer segments 24 form electrical capacitors with a certain capacitance C. In a plate-shaped configuration of the ultrasonic transducer 22, the above-mentioned condition is generally satisfied if the different transducer segments 24, 24', 24'' etc. have the same surface.

Figure 6:
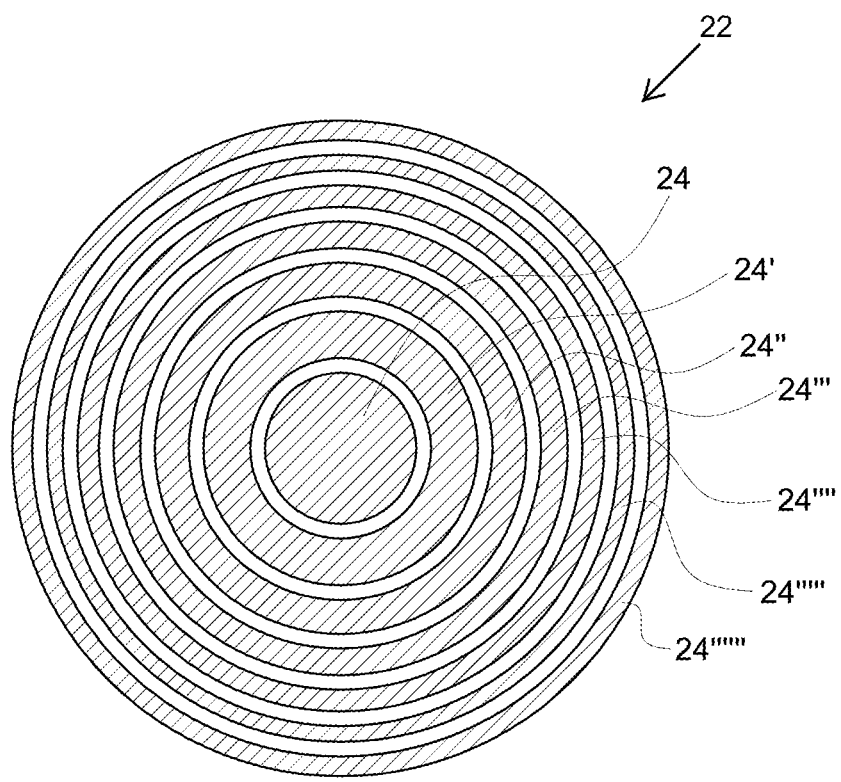
FIG. 6: shows a top view of the ultrasonic transducer according to a second preferred exemplary embodiment of an ultrasonic test probe according to the invention.

FIG. 6 shows a second exemplary embodiment of an ultrasonic transducer 22 whose individual transducer segments 24, 24', 24'' etc. have a ring thickness Si that decreases in an outward direction, so that the surfaces F1, F2, F3, . . . of the transducer segments 24, 24', 24'', 24''', . . . are substantially identical. This special ring configuration is also known from optics as a "zone plate" and has the particular advantage that all the transducer segments transmit with the same amplitude if activated in parallel.

If, on the other hand, it is intended to accomplish that the thickness si of the sectors Ri that can be inspected with the method according to the invention is substantially constant, then it has to be ensured that the near-field length N increases in a linear manner with i when transitioning from any effective ultrasonic transducer 22$i$ formed by the group i of transducer segments 24 to the effective ultrasonic transducer 22 (i+1) formed by the group (i+1) of transducer segments 24. Because of the correlation $$N = \frac{D^2}{4\lambda},$$

this is satisfied exactly if, during a transition from the ultrasonic transducer 22$i$ to the ultrasonic transducer 22($i$+1), the diameter is substantially proportional to the square root of i. The ring thickness S, S', S'', S''', . . . of the successive transducer segments 24, 24', 24'', 24''' . . . can be directly determined from this in another preferred embodiment of an ultrasonic test probe not shown in the Figures.

Figure 7:
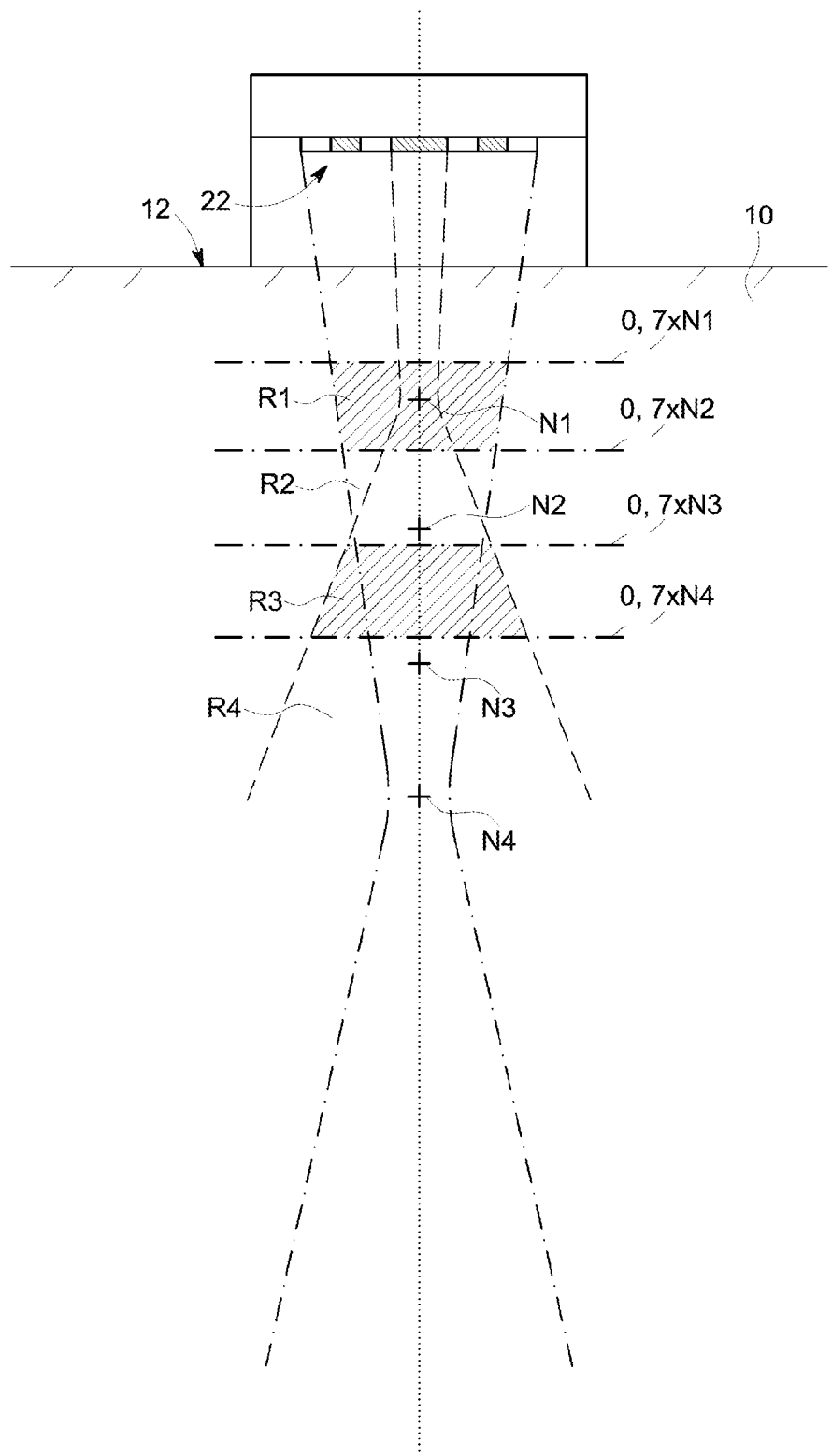
FIG. 7: shows an enlarged detail in analogy to the illustration of FIG. 3, but for the ultrasonic test probe according to the second exemplary embodiment.

However, the annular transducer segments 24, 24', 24'', 24''' . . . determined under the above-mentioned condition do not have the same surface F, F', F'', F''' . . . . Therefore, the further criterion that the capacitance of the individual transducer segments 24 is supposed to be substantially the same is not satisfied in this case. However, this criterion can be satisfied by the individual circular or annular transducer segments 24 being again subdivided into smaller, individually activatable transducer elements 25, all of which in that case have substantially the same surface and thus the same capacitance. Such an ultrasonic transducer 22 in accordance with this third preferred exemplary embodiment is shown schematically in FIG. 7. In practice, a subdivision of the individual transducer segments 24 into significantly smaller transducer elements 25 will be necessary in order to be able to satisfy the additional criterion of identical surfaces of the transducer elements 24 with sufficient accuracy.

Figure 8:
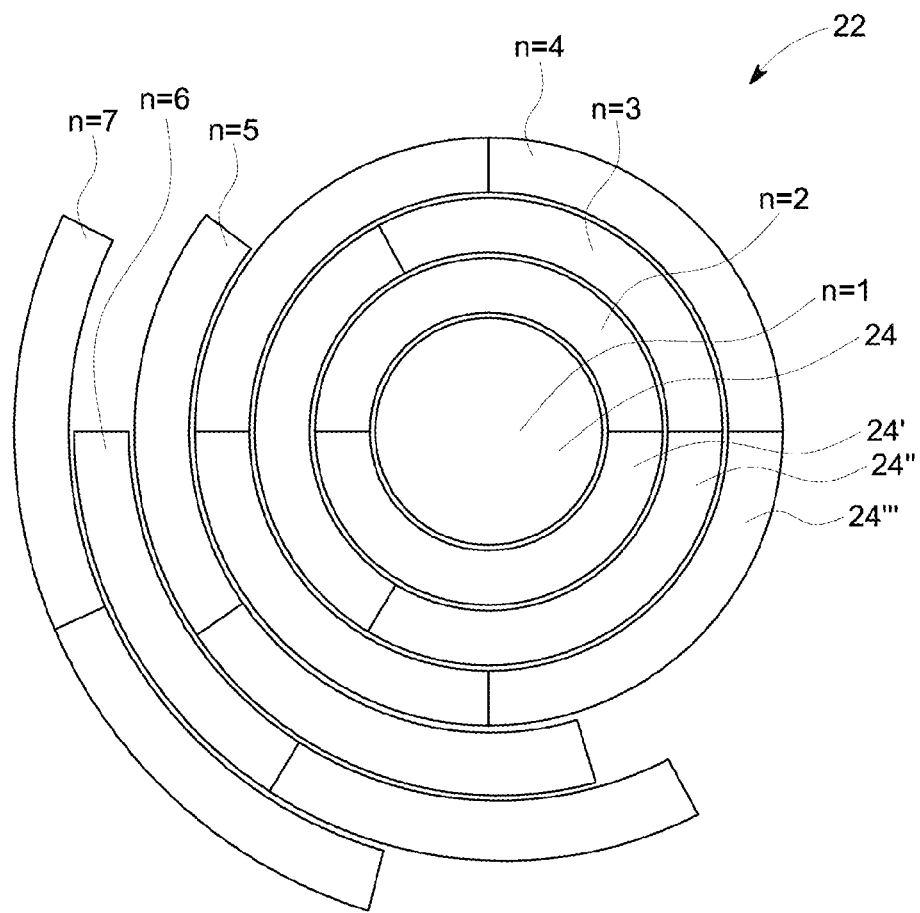
FIG. 8: shows a top view of the ultrasonic transducer according to a third preferred exemplary embodiment of an ultrasonic test probe according to the invention.

The division of the volume of the test object 10 into sectors R1, R2, R3, ... which results if such a ultrasonic transducer 22 is used is indicated by way of example in FIG. 8. It is apparent from it that the individual sectors R1, R2, ... substantially all have the same thickness. Thus, a consistent resolution can be achieved virtually over the entire thickness S of the test object 10. At the same time, the ultrasonic field generated by the transducer groups i, j, ... is substantially identical with the ultrasonic field generated by a circular ultrasonic transducer with the respectively same diameter.

I claim:

1. Method for the non-destructive inspection of a test object (10) with a great material thickness by means of ultrasound comprising the following method steps:
  a. providing an ultrasonic test probe (20) with an ultrasonic transducer (22) divided into a plurality of individually activatable transducer segments (24), wherein the transducer segments (24) are concentric circles or rings, or sections thereof, characterized in that the transducer segments (24) are dimensioned in such a way that the diameter Dm of the circular active surface Fm of the ultrasonic transducer (22) formed by a group i (i=1, 2, 3, ...) of transducer segments (24) is substantially proportional to the square root of i,
  b. selecting a first group j (j=1, 2, 3, ...) of transducer segments (24) in such a way that a parallel activation of these transducer segments (24) results in a circular active surface Fj of the ultrasonic transducer (22), and
  c. carrying out an ultrasound inspection of the test object (10) with the first group j (j=1, 2, 3, ...) of transducer segments (24), wherein they are being activated in parallel;
  characterized in that a predetermined criterion K has to be satisfied when the method is being carried out which is dependent upon the ultrasonic field that is generated by the active surface Fj of the ultrasonic transducer (22), comprising the following further method steps:
  selecting the first group j (j=1, 2, 3, ...) of transducer segments that are activated in parallel in such a way that the ultrasonic field generated by the active surface Fj of the ultrasonic transducer (22) satisfies the criterion K;
  wherein the criterion K is satisfied if:

$$dj \geq 0.7 \times Nj$$

applies, with dj being the minimum distance of the sector Rj to be inspected from the coupling location (14) of the ultrasound into the test object along the sound path in the test object (10) and Nj being the near-field length of the active surface Fj of the ultrasonic transducer (22) formed by the first group j (j=1, 2, 3, ...) of transducer segments (24).

2. Method according to claim 1, characterized by the following further method steps:
  a. selecting a sector Rj to be inspected of the test object (10),
  b. selecting the first group j (j=1, 2, 3, ...) of transducer segments that are activated in parallel in such a way that the ultrasonic field in the sector Rj generated by the active surface Fj of the ultrasonic transducer (22) satisfies the criterion K.

3. Method according to claim 2, characterized by the following further method steps:
  a. presetting a material thickness S to be inspected of the test object (10),
  b. dividing the material thickness S to be inspected of the test object (10) into a plurality of sectors Ri (i=1, 2, 3, ...) disposed one behind the other in the ultrasound propagation direction in the test object (10),
  c. selecting the sector Rj to be inspected from amongst the sectors Ri.

4. Method according to claim 1, characterized in that the ultrasound inspection is carried out in accordance with the DGS method.

5. Method according to claim 4, characterized in that the specific DGS diagram (34j) for the ultrasonic transducer (22) having the circular active surface Fj formed by the selected group j of transducer segments (24) is computed from the general DGS diagram (34).

6. Method according to claim 1, characterized in that the ultrasound inspection is carried out in accordance with the DAC method.

7. Method according to claim 1, characterized in that the method is carried out for different sectors Rj,k.

8. Method according to claim 7, characterized in that the sectors Rj,k have substantially the same extent in the sound propagation direction.

9. Method according to claim 7, characterized in that electronic screens are used for acquiring different sectors Ri,j of the test object (10).

10. Method according to claim 7, characterized in that the first and second ultrasound inspections are carried out from the same coupling location (14).

11. Method according to claim 1, characterized in that the transducer segments (24) of the ultrasonic transducer (22) of the provided ultrasonic test probe (20) are dimensioned in such a way that the diameter Dm of the circular active surface Fm of the ultrasonic transducer (22) formed by a selected group i of transducer segments (24) is substantially proportional to the square root of i.

12. Method according to claim 1, characterized in that the transducer segments (24) have substantially the same surface f.

13. Ultrasonic test probe (20) according to claim 1, characterized in that the transducer segments (24) have substantially the same surface f.

14. Control unit (30) for an ultrasonic test probe (20) for the non-destructive inspection of a test object (10) with a great material thickness by means of ultrasound, wherein the ultrasonic test probe (20) comprises an ultrasonic transducer (22) divided into a plurality of individually activatable transducer segments (24), wherein the transducer segments (24) are concentric circles or rings, or sections thereof, characterized in that the control unit (30) is configured to activate in parallel a first group j (j=1, 2, 3, ...) of transducer segments (24) in such a manner that the result is a circular active surface Fj of the ultrasonic transducer (22), characterized in that the transducer segments (24) are dimensioned in such a way that the diameter Dm of the circular active surface Fm of the ultrasonic transducer (22) formed by a group i (i=1, 2, 3, . . . ) of transducer segments (24) is substantially proportional to the square root of i;

characterized in that the control unit:
a. is configured for executing an ultrasonic inspection method during whose execution a predetermined criterion K has to be satisfied which is dependent upon the ultrasonic field that is generated by the active surface Fj of the ultrasonic transducer (22), and
b. is configured to select a first group j (j=1, 2, 3, . . . ) of transducer segments (24) whose parallel activation results in a circular active surface Fj of the ultrasonic transducer (22), wherein the ultrasonic field generated by the active surface Fj of the ultrasonic transducer (22) satisfies the criterion K;

wherein the criterion K is satisfied if:

$$dj \geq 0.7 \times Nj$$

applies, with dj being the minimum distance of the sector Rj to be inspected from the coupling location (14) of the ultrasound into the test object along the sound path in the test object (10) and Nj being the near-field length of the active surface Fj of the ultrasonic transducer (22) formed by the first group j (j=1, 2, 3, . . . ) of transducer segments (24).

15. Device (1) for the non-destructive inspection of a test object (10) by means of ultrasound, characterized in that the device (1) comprises the following:
a. an ultrasonic test probe (20) with an ultrasonic transducer (22) divided into a plurality of individually activatable transducer segments (24), wherein the transducer segments (24) are concentric circles or rings, or sections thereof, and
b. a control unit (30) according to claim 14.

* * * * *